United States Patent [19]

Daniel et al.

[11] Patent Number: 5,114,419
[45] Date of Patent: May 19, 1992

[54] HYGIENIC DEVICE

[76] Inventors: Sarah Daniel, Betzalel Linda 3, Rehovot; Dan Lewinthal, Moshav Asseret 119; Jacques Daniel, Betzalel Linda 3, Rehovot, all of Israel

[21] Appl. No.: 430,714

[22] Filed: Nov. 2, 1989

[51] Int. Cl.$^5$ .................. A61F 13/15; A61F 13/00; A41B 9/08
[52] U.S. Cl. .................. 604/385.1; 128/891; 2/402
[58] Field of Search .............. 450/97, 100, 104, 153, 450/154; 2/267, 272, 46, 400, 78 R, 402; 604/359, 304, 307, 385.1, 393, 394, 401, 402; 128/577, 887-891

[56] References Cited

U.S. PATENT DOCUMENTS

| | | | |
|---|---|---|---|
| 673,630 | 5/1901 | Warner | 604/304 |
| 2,951,481 | 9/1960 | Gordon | 2/403 X |
| 3,092,103 | 6/1963 | Mower | 128/163 X |
| 3,339,208 | 9/1967 | Marbach | 2/403 X |
| 3,973,561 | 8/1976 | Kane | 128/163 X |
| 4,019,517 | 4/1977 | Glassman | 604/359 X |
| 4,237,591 | 12/1980 | Ginocchio | 604/359 X |
| 4,363,322 | 12/1982 | Andersson | 604/359 |
| 4,616,643 | 10/1986 | Jung | 128/886 |
| 4,617,230 | 10/1986 | Shah et al. | 604/359 X |
| 4,660,229 | 4/1987 | Harris | 2/209 |
| 4,743,249 | 5/1988 | Loveland | 604/304 X |
| 4,753,643 | 6/1988 | Kassai | 604/359 |
| 4,808,174 | 2/1989 | Sorkin | 604/352 X |
| 4,842,593 | 6/1989 | Jordan et al. | 604/360 |
| 4,856,534 | 8/1989 | Sorkin et al. | 604/352 X |
| 4,888,007 | 12/1989 | Loeb et al. | 604/352 |
| 4,894,869 | 1/1990 | Boll | 2/400 |
| 4,904,251 | 2/1990 | Igaue et al. | 604/385.2 |
| 4,907,579 | 3/1990 | Kum | 604/304 X |
| 5,069,228 | 12/1991 | Sorkin | 604/352 X |

FOREIGN PATENT DOCUMENTS

| | | | |
|---|---|---|---|
| 0248173 | 9/1987 | European Pat. Off. | 2/402 |
| 2626446 | 8/1989 | France | 2/46 |

*Primary Examiner*—David Isabella
*Assistant Examiner*—Elizabeth M. Burke
*Attorney, Agent, or Firm*—Ostrolenk, Faber, Gerb & Soffen

[57] ABSTRACT

A hygienic device for protecting the genital, urinary and rectal areas of human beings during bathing and swimming activities as disclosed. The device is intended for protecting said areas against irritation, inflammation or infection. It is made of a flexible, thermoplastic and impermeable material and shaped to closely adhere to said areas by all its edges.

18 Claims, 1 Drawing Sheet

HYGIENIC DEVICE

FIELD OF INVENTION

The present invention relates to a new hygienic device for preventing and protecting various parts of human or animal body from the contaminating environmental agents comprising at least one layer of a sheet of impermeable material shaped to cover and isolate said parts from said contaminating environmental agents.

More particularly it relates to infection and irritation preventing device made from a thermoplastic waterproof material shaped to cover and adhere by all its edges to the parts of the body needing protection from pathogens and irritating agents affecting genital, urinary or anorectal areas found in bathing places or other indoor and outdoor facilities.

The present invention further includes an inner layer of an absorbent non-irritating, non-allergic soft cloth treated by a suitable composition to prevent the growth or migration of said pathogens inside said parts.

TECHNICAL BACKGROUND AND SUMMARY OF THE INVENTION

For all segments of the population bathing in swimming pools, lakes, seas, walking or seating on public grounds etc. involves a risk of contamination by various pathogens and other contaminants and irritating agents and especially those affecting the genital, urinary and anorectal regions. For example, the risk of infection could persist despite the use of antiseptic agents in water, recreation centers, and other outdoors. The health hazard associated with bathing has been further aggravated these last decades by the ever-increasing number of bathers and recreation centers around the world. Therefore, more efficient and individual protecting devices for the human population as well as animal breeding against possible contaminating environmental agents originating from various recreation areas and especially from bathing activities, are highly desirable.

Healthy population needs a device which is discreetly and adequately shaped, but is also effectively isolating the most exposed parts from the contaminating environments without adversely affecting the comfort of their usual activities. There is no such cloth or other kind of convenient spacer material on the market which is protective of various orifices in the human and animal body from the pathogens present in most public and private places.

A hygienic slip for wearing when trying on articles of clothing such as lingerie or bathing costumes prior to purchase made of thin, flexible, impermeable film is disclosed in European Patent Application 0248173. Moreover, this above disclosed diabolo-shaped panel may be used as disposable accessories in clothing shops to allow a person to try on, e.g. underwear but it is attached only by its corners either via self-adhesive strips or coated patches adherent to user's skin. Obviously, this hygienic protective device cannot be used to isolate the user's parts of the body from the contaminating environmental agents and from pathogens and other irritating agents which can penetrate through the non-adherent edges and easily enter open orifices.

This is why the present inventors have found that the use of especially shaped material, hermetically sealed to the user's skin is the most appropriate device to protect said parts from the outside aggression by water, soil or air.

This is the object of the present invention to provide an impermeable, thermoplastic material such as latex, device having a flexible outer layer which is in contact with the contaminating environments and having optionally an inner layer of soft, absorbent non-irritating cloth, which covers and isolates the part of the body and prevents its infection or irritation. Said inner layer may be treated by suitable composition to prevent growth and migration.

It is another object of this invention to provide a device with a self-adhesive material located at its edges or coated to be adherent to the user's body excluding the penetration of pathogens or irritants from contaminating environments.

It is a further object of the present invention to provide various forms for said device, which can be triangular, circular, rectangular or annular. It could take a form of a spacer which may be convex or concave. It may be used as slip, short, bermuda, panties, pouch or another shape compatible with the part of the body which needs said protection.

The device may be disposable or washable offering a repeated use and longer duration, if necessary.

DETAILED DESCRIPTION OF THE INVENTION AND FIGURES

Figure 1:
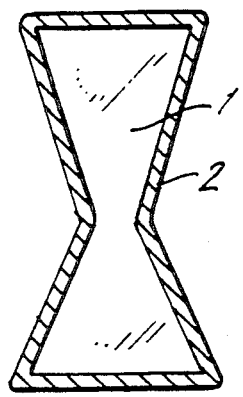

By way of examples, illustrated in the FIGS. 1 to 8, the present invention can be described as follows: FIGS. 1 and 3 show said hygienic device having one layer of resistant, flexible, thermoplastic and impermeable material (1) hour-glass bi-concave shaped to be preferably used as an underwear. It preferably has self-adhesive strips (2) applied along its edges to closely adhere to the lower abdomen, pubis perineum and sacrum skin.

These strips may optionally be coated to hermetically seal the edges of the above underwear or be glued to its edges by a water resistant and non-irritating glue. It should preferably be made from material able to maintain its sealing properties for a sufficient period of time.

These self-adhesive strips shall offer the possibility to use said device several times without losing its adhering and sealing properties. They should be large enough with variable width and length to be appropriate for the shape and kind of the said protected part of the body. It should preferably be comfortable and avoid pain sensation during its use without losing its efficiency in isolating said part from contaminating environmental agents.

The shape illustrated by FIGS. 1 and 3 may be formed by two widening portions, one in front covering, for example, the pubic area and the other side, at the back covering the sacral area, both portions connected by a narrower band covering in between perineum. The front and rear parts of said device may be symmetrical or asymmetrical, having triangle-like edges as shown in FIG. 1 or having round, concave, convex or mixed edges.

Figure 2:
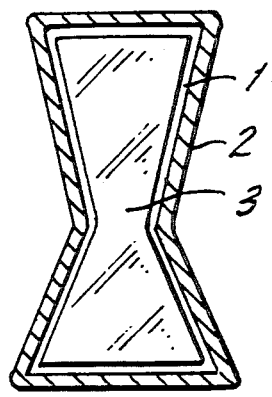
Figure 3:
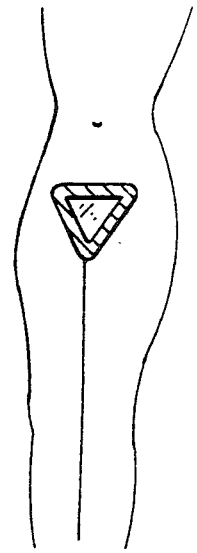

FIG. 2 shows another feature of the embodiment described above in FIG. 1, it is comprising an optional inner layer made of sheet of material which is a soft, non-irritating and non-allergic cloth or sponge. It may preferably be absorbent and treated by suitable composition to increase said protection from contamination or irritation by the environmental agents. It may be also treated by fungicide or antiseptic agent and absorb internal secretions or to serve as deodorant.

Figure 4:
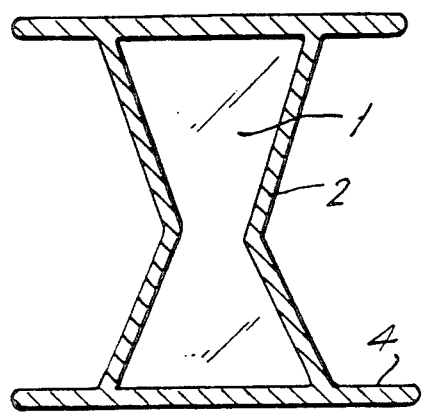
Figure 5:
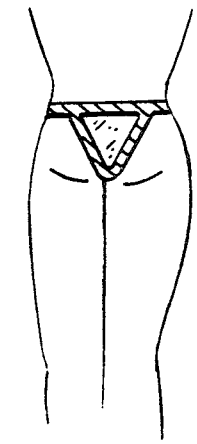

FIGS. 4 and 5 illustrate another feature comprising additional sealing straps (4) which may be crossed or attached and which are the prolongation of the self-adhesive strips (2) applied along the edges of said device, as described in the above FIGS. 1 and 3.

Figure 6:
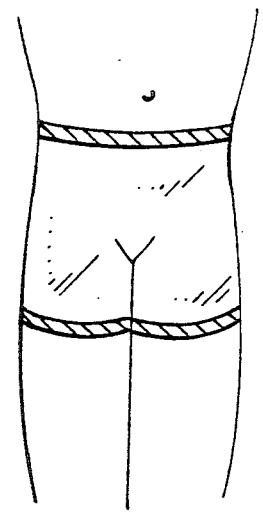
Figure 7:
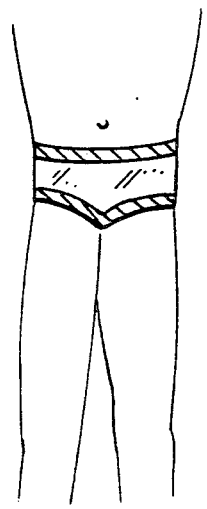
Figure 8:
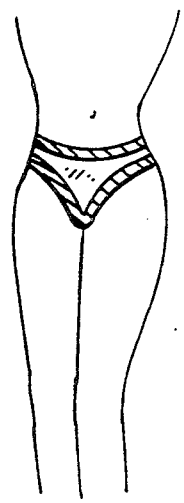

FIGS. 6, 7 and 8 provide examples of various shapes and forms (slip, panties and short, etc.) that may be used in accordance with the present invention.

Said hygienic device may be made in different colors, and designs to increase its aesthetic and commercial appeal. It may be transparent or opaque, shaped as a cloth of different sizes and dimensions to fit the various parts of human and animal body such as genital, urinary, rectal, ears, nose, toes, hands, etc.

Although the invention has been described with reference to particular means it is to be understood that the invention is not limited to the particulars disclosed and extends to all equivalents falling within the scope of the claims.

We claim:

1. Hygienic device for protecting the genital, urinary and rectal parts of the human body against environmental agents causing irritation, inflammation and/or infection during bathing or swimming, which is made from flexible, thermoplastic and liquid impermeable material and having a shape with a periphery defined by outer edges which covers and closely adheres to said parts by all said edges, the hygienic device having body adhering water resistant, non-irritating adhesive means at all of said edges operative to hermetically seal all of said parts from an outside contaminated liquid environment and having an inner layer which is soft, non-irritating and non-allergic cloth or sponge.

2. The device according to claim 1 wherein said material is made of latex.

3. The device according to claim 1 wherein said material is elastic.

4. The device according to claim 1 wherein said material is transparent.

5. The device according to claim 1 wherein said material is colored and/or containing a design.

6. The device according to claim 1 wherein said inner layer of sheet of material is absorbent.

7. The device according to claim 6 wherein said sheet of material is treated by suitable composition to prevent growth and/or migration of pathogens or agents inside said parts.

8. The device according to claim 7 wherein said composition is an antiseptic agent.

9. The device according to claim 6 wherein said sheet of material is treated by a deodorant.

10. The device according to claim 6 wherein said sheet of material is able to absorb internal secretions of said parts.

11. The device according to claim 1 wherein said material is shaped in triangular, rectangular, circular or annular form.

12. The device according to claim 1 wherein said form is an underwear, slip, panties, short, bermuda or pouch.

13. The device according to claim 1 wherein said sheet of material is shaped as a garment.

14. The device according to claim 1 which is disposable.

15. The device according to claim 1 which is washable and reusable.

16. The device according to claim 1 wherein a self adhesive strips are applied on all the edges of said material to be closely adherent to said parts.

17. The device according to claim 16 wherein a water resistant glue is applied along said edges.

18. The device according to claim 16 wherein said strips are coated to be closely adherent to said parts.

* * * * *